United States Patent [19]

Sundt

[11] Patent Number: 4,878,900
[45] Date of Patent: Nov. 7, 1989

[54] SURGICAL PROBE AND SUCTION DEVICE

[76] Inventor: Thoralf M. Sundt, Dept. of Neurosurgery, Mayo Clinic, Rochester, Minn. 55905

[21] Appl. No.: 224,943

[22] Filed: Jul. 27, 1988

[51] Int. Cl.⁴ ............................................. A61M 1/00
[52] U.S. Cl. .................................. 604/119; 604/283; 604/902; 433/91; 285/921
[58] Field of Search ............... 604/119, 266, 268, 283, 604/902, 35, 73, 93, 118, 119, 187, 240, 243, 264–269, 275, 276; 433/91–96; 285/33, 34, 921

[56] References Cited

U.S. PATENT DOCUMENTS

| | | | |
|---|---|---|---|
| 1,583,023 | 5/1926 | Stoloff | 433/93 |
| 2,531,730 | 11/1950 | Henderson | 604/902 |
| 2,711,586 | 6/1955 | Groves | 433/95 |
| 3,335,727 | 8/1967 | Spoto | 604/119 |
| 3,516,160 | 6/1970 | Leffler | 433/95 |
| 3,713,443 | 1/1973 | Fertik | 604/119 |
| 3,848,604 | 11/1974 | Sackner | 604/119 |
| 4,068,664 | 1/1978 | Sharp et al. | 604/902 |
| 4,083,115 | 4/1978 | McKelvey | 433/96 |
| 4,205,677 | 6/1980 | Engstrom | 604/119 |
| 4,299,221 | 11/1981 | Phillips et al. | 604/119 |

Primary Examiner—Stephen C. Pellegrino
Assistant Examiner—Ralph Lewis
Attorney, Agent, or Firm—Burd, Bartz & Gutenkauf

[57] ABSTRACT

A probe and suction device for use during surgery is disclosed. The device includes an elongated tubular handle adapted for connection to a source of suction and a separable elongated tubular probe and suction member. It includes a suction regulating orifice in the handle and is characterized by a positive snap-on rotatable connection between the handle and the probe and suction member. The digital end of the probe and suction member is blunted to avoid tissue damage.

14 Claims, 2 Drawing Sheets

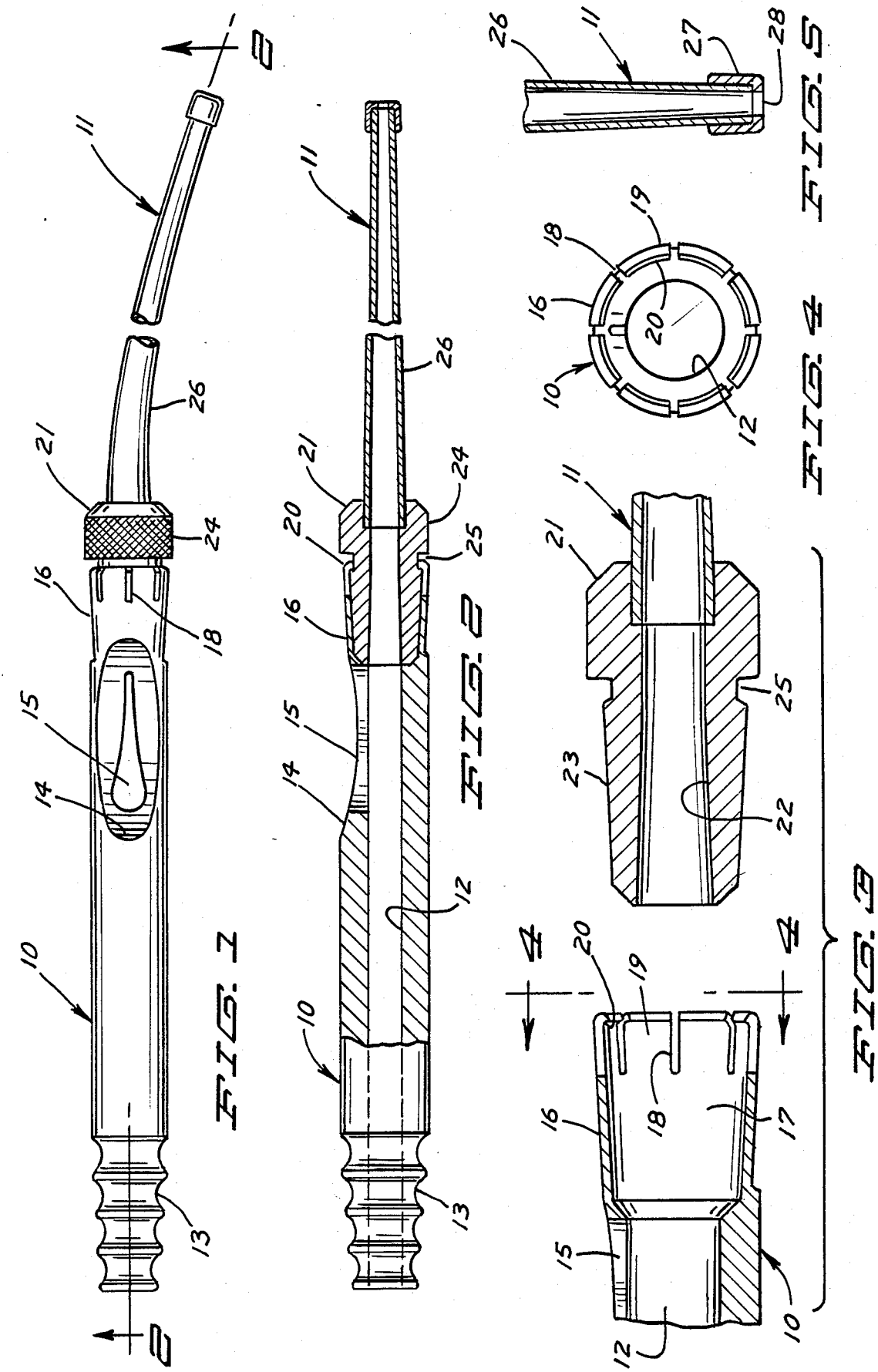

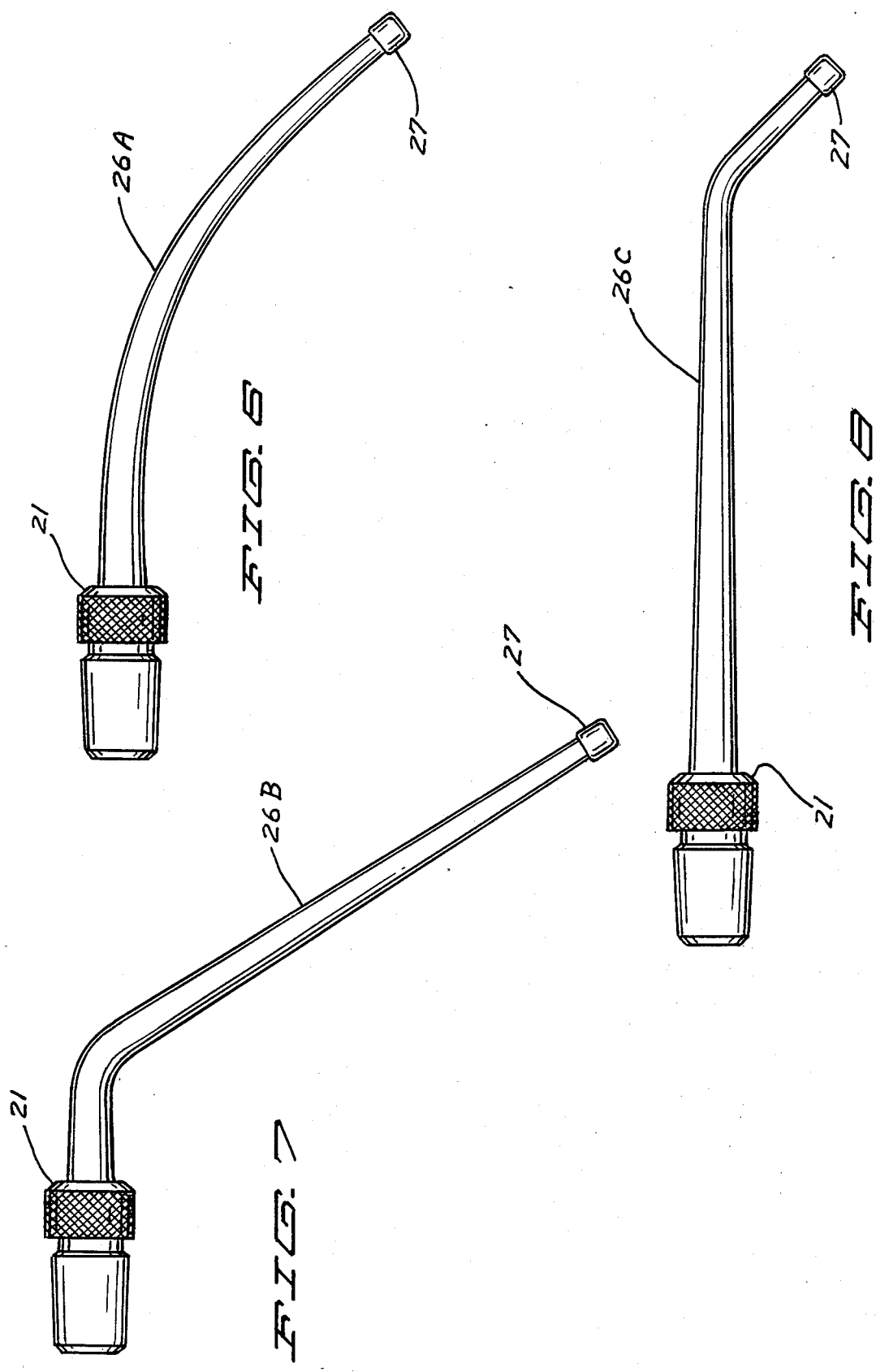

SURGICAL PROBE AND SUCTION DEVICE

BACKGROUND OF THE INVENTION

1. Field of the Invention

This invention is directed to a probe and suction device for use by surgeons to remove blood, fluid and debris from the surgical site and to permit the surgeon to probe within the surgical site. More particularly, the invention is directed to a surgical probe and suction device characterized by adjustable suction and interchangeable freely rotatable positive snap-on elongated tubular probes and suction members of various configurations.

2. The Prior Art

Although surgical probes and suction devices having means for variation of the suction are known, these are rigid one-piece instruments having straight-line elongated probe and suction members and requiring replacement of the entire instrument to change the size or length of the probe and suction members. The distal ends of these instruments tend to be sharp and capable of injury to delicate tissue.

SUMMARY OF THE INVENTION

The present invention overcomes the limitations and disadvantages of the prior art instruments. Broadly stated, the present invention comprises a surgical probe and suction device having an elongated tubular handle with a central longitudinal passage and having means at one end adapted for connection to a vacuum source. The handle includes a suction regulating orifice communicating with the central passage. An elongated tubular probe and suction member is connected to the end of the handle opposite from the connection to the vacuum source. A positive snap-on rotatable connection is provided between the handle and the probe and suction member for easy interchange of different probe and suction members on the same handle. Each probe and suction member is provided with a blunted distal end. The snap-on rotatable connection includes a tapered male connection member having a central passage and an annular groove around its outer periphery spaced from the end, and a mating female connection member. The female connection member includes an annular ring surrounding a central passage and having a plurality of resilient finger members, each having an inwardly directed lip adapted to engage the annular groove around the male connecting member.

BRIEF DESCRIPTION OF THE DRAWINGS

The invention is illustrated by the accompanying drawings in which corresponding parts are identified by the same numerals and in which:

FIG. 1 shows a top plan view of an assembled probe and suction device according to the present invention;

FIG. 2 is an elevation in section of the assembled unit;

FIG. 3 is an enlarged fragmentary section showing in exploded view the snap-on rotatable connection between the handle and probe and suction member;

FIG. 4 is an end elevation of the female connection member on the line 4—4 of FIG. 3 and in the direction of the arrows;

FIG. 5 is an enlarged sectional view of the blunted tip of the probe and suction member; and FIGS. 6 through 8 are elevations showing three of many varying configurations of probe and suction members.

DETAILED DESCRIPTION OF THE PREFERRED EMBODIMENT

Referring now to the drawings, and particularly to FIGS. 1 and 2, there is shown a surgical probe and suction device according to the present invention including a handle, indicated generally at 10, and a replaceable interchangeable probe and suction member, indicated generally at 11. Handle 10 is elongated, rigid and tubular having a central longitudinal passage 12 extending throughout its length. The proximal or near end of the handle is provided with a tapered nipple-like fitting 13 adapted for engagement with the end of a flexible hose or tube which in turn is connected to a vacuum source, such as a suction pump or the like. The outer surface of handle 10 is preferably knurled for positive non-slip handling by the surgeon.

As is known in the art, one side of the handle adjacent to the distal or far end of the handle is provided with a shallow concave surface 14 surrounding a radial slot or orifice 15 communicating with the handle central passage 12. The orifice 15 desirably has the shape of an elongated tear-drop with the larger portion toward the proximal end of the handle. Suction to the probe and suction member is regulated by the surgeon through placement of a thumb or finger over the concavity 14 and positioning to cover as much of orifice 15 as will provide the desired suction.

The distal end of handle 10 is provided with a female connection member 16. As best seen in FIG. 3, the female connection member 16 has a central passage 17 which is part of passage 12 through the handle. Passage 17 is tapered, larger near the distal end of the handle. The distal end of female connection member 16 is provided with a plurality of parallel, uniformly spaced, longitudinally extending, radial slots 18, here shown (FIG. 4) as eight in number. The slots 18 in turn define a plurality of parallel resilient closely spaced apart finger members 19, each of which is provided with a radially inwardly extending lip 20.

Each probe and suction member 11 has a hub or cone section 21 at its proximal end. Cone 21 has a central longitudinal passage 22. Passage 22 is preferably tapered, as a Luer taper, to receive the tip or nozzle of a syringe to permit flushing of the probe and suction member. Cone 21 comprises a male connection member adapted for engagement with female connection member 16. The proximal end 23 of cone 21 is tapered to fit with a slide fit within tapered passage 17 of the female connection member. The distal end 24 is of slightly larger diameter than the widest end of tapered male connection member 23, and its outer surface is preferably knurled for positive non-slip grasping by the surgeon or other operating room personnel. An annular groove 25 is provided in the outer surface of cone 21 adjacent to the tapered male connection member 23. As best seen in FIG. 2, when the probe and suction member 11 is in engagement with handle 10, lips 20 of the female connection member 16 engage annular groove 25. This permits positive snap-on connection between the handle and probe and suction member which may be felt and/or heard. The engagement between lips 20 and groove 25 permit the probe and suction member to be firmly engaged by the handle while permitting the probe and suction member to be freely rotated relative to the handle. At the same time, only slight force is required to disengage the probe and suction member from the handle for interchange of a different member.

The probe and suction member 11 includes an elongated tubular section 26, preferably tapered from largest at its proximal end which is inset into cone section 21 and welded or otherwise securely held. The central passage of tubular section 26 communicates directly with passages 12 and 22 through the handle and cone. The tubular section may have a variety of different configurations as shown at 26A, 26B and 26C in FIGS. 6 through 8, respectively, depending upon the needs and desires of the surgeon. Because of the ready interchangeability of the probe and suction members, change may be quickly and easily made during surgery, as desired.

To avoid damage to delicate tissue by the tubular section of the probe and suction member, its tip end is desirably blunted. Preferably this is done by providing an enlarged tip 27 of synthetic resinous material. A preferred material is polytetrafluoroethylene (Teflon), applied by dipping tubular section 26 into a fluid plastic bath with a mandrel in place to prevent clogging of the tubular section. After setting of the plastic tip and withdrawal of the mandrel, the passage 28 is preferably drilled to insure a clean open passage.

The surgical probe and suction device of this invention may be manufactured for repeated use. In this instance, it is constructed from high strength, long-life material, bio-compatible, non-toxic to body tissues and readily sterilizable, such as surgical grades of stainless steel, or the like. Alternatively, the device, particularly the probe and suction member thereof, may be made of non-toxic bio-compatible sterilizable resinous plastic materials for disposal after each use. Although the device is described and illustrated as having the female connection member on the handle and the male connection member on the probe and suction member, it is apparent that these relationships may be reversed.

In use, the instrument is connected to a vacuum source. It is grasped by the surgeon as most comfortable with a thumb or finger wholly or partially overlying suction regulating orifice 15. The tip of the instrument is placed in collected pools of blood, fluid and debris within the surgical site and that blood is removed. The tip of the probe may be maneuvered to explore the surgical site as necessary.

It is apparent that many modifications and variations of this invention as hereinbefore set forth may be made without departing from the spirit and scope thereof. The specific embodiments described are given by way of example only and the invention is limited only the terms of the appended claims.

I claim:

1. A surgical probe and suction device comprising:
   (A) an elongated tubular handle having a central longitudinal passage and means at one end for connection to a vacuum source,
   (B) a suction regulating orifice in said handle communicating with said central passage,
   (C) a separable elongated tubular probe and suction member connected to the opposite end of said handle and having an open passage therethrough,
   (D) a positive snap-on rotatable connection between said handle and probe and suction member, said connection comprising:
      (1) a tapered male connection member extending from the probe or the handle having a central passage therethrough,
      (2) an annular groove around said male connection member spaced from the end thereof,
      (3) a mating female connection member adapted to receive and engage said male connection member extending from the other of said probe or handle and comprising:
         (a) an annular ring having a plurality of parallel resilient finger members closely and uniformly spaced apart about a central passage, and
         (b) an inwardly directed lip at the ends of each of said finger members adapted to engage the annular groove around said male connection member, and
   (E) a blunted distal end on said probe and suction member surrounding the open passage therein.

2. A surgical probe and suction device according to claim 1 wherein:
   (A) said female connection member is at the distal end of said handle, and
   (B) said male connection member is at the proximal, end of said probe and suction member.

3. A surgical probe and suction device according to claim 2 wherein the central passage through the male connection member has a Luer taper at its proximal end to facilitate flushing debris from the tip of the probe and suction member.

4. A surgical probe and suction device according to claim 1 wherein said elongated probe and suction member is tapered from wider at its proximal end to narrower at its distal end.

5. A surgical probe and suction device according to claim 1 wherein said blunted distal end of said probe and suction member comprises a synthetic resinous coating around the annular end edge and adjacent exterior side wall of said probe and suction member.

6. A surgical probe and suction device according to claim 5 wherein said synthetic resinous coating is polytetrafluoroethylene.

7. A surgical probe and suction device according to claim 1 wherein said suction regulating orifice comprises a tapered elongated slot in the wall of the handle widest at the proximal end and narrowest at the distal end.

8. A surgical probe and suction device comprising:
   (A) an elongated tubular handle having a central longitudinal passage and a fitting at its proximal end for connection to a vacuum source,
   (B) a suction regulating orifice in said handle adjacent to the distal end and communicating with said central passage,
   C) a separable elongated tapered tubular probe and suction member connected to the distal end of said handle, said member having an open passage therethrough and being widest at its proximal end,
   (D) a blunted distal end on said probe and suction member surrounding the open passage therethrough, and
   (E) a positive snap-on rotatable connection between said handle and said probe and suction member comprising:
      (1) a tapered male connection member extending from the probe or the handle having a central passage therethrough,
      (2) an annular groove around said male connection member spaced from the narrower end thereof, (3) a mating female connection member extending from the other of said probe or handle adapted to receive and engage said male connection member and comprising:
  (a) an annular ring having a plurality of parallel resilient finger members closely and uniformly spaced apart about a central passage, and
  (b) an inwardly directed lip at the ends of each of said finger members adapted to engage the annular groove around the male connection member.

9. A surgical probe and suction device according to claim 8 wherein:
  (A) said female connection member is at the distal end of said handle, and
  (B) said male connection member is at the proximal end of said probe and suction member.

10. A surgical probe and suction device according to claim 9 wherein the central passage through the male connection member has a Luer taper at its proximal and to facilitate flushing debris from the tip of the probe and suction member.

11. A surgical probe and suction device according to claim 8 wherein said blunted distal endof said probe and suction member comprises a synthetic resinous coating around the annular end edge and adjacent exterior side wall of said probe and suction member.

12. A surgical probe and suction device according to claim 11 wherein said synthetic resinous coating is polytetrafluoroethylene.

13. A surgical probe and suction device according to claim 8 wherein said suction regulating orifice comprises a tapered elongated slot in the wall of the handle widest at the proximal end and narrowest at the distal end.

14. A surgical probe and suction device according to claim 8 wherein said handle, said probe and suction member and said connection are composed of surgical grade stainless steel and the exterior of said handle is knurled.

* * * * *

UNITED STATES PATENT AND TRADEMARK OFFICE
CERTIFICATE OF CORRECTION

PATENT NO. : 4,878,900

DATED : November 7, 1989

INVENTOR(S) : THORALF M. SUNDT

It is certified that error appears in the above-identified patent and that said Letters Patent is hereby corrected as shown below:

Abstract, line 8, "digital" should be --- distal ---.

Col. 4, lines 6 through 9, should read:

--- (3) a mating female connection member extending from the other of said probe or handle adapted to receive and engage said male connection member and comprising: ---

Col. 5, line 21, "and" should be --- end ---.

Col 6, line 4, "endof" should be --- end of ---.

Signed and Sealed this

Tenth Day of March, 1992

Attest:

HARRY F. MANBECK, JR.

*Attesting Officer*  *Commissioner of Patents and Trademarks*